United States Patent
Lechot (10) Patent No.: US 7,229,078 B2
(45) Date of Patent: Jun. 12, 2007

(54) HOLLOW SMALL DIAMETER TOOL HOLDER FOR SURGICAL USE

(75) Inventor: André Lechot, Orvin (CH)

(73) Assignee: Precimed S.A., Orvin (CH)

( * ) Notice: Subject to any disclaimer, the term of this patent is extended or adjusted under 35 U.S.C. 154(b) by 0 days.

(21) Appl. No.: 10/901,012

(22) Filed: Jul. 28, 2004

(65) Prior Publication Data

US 2005/0131395 A1 Jun. 16, 2005

Related U.S. Application Data (63) Continuation-in-part of application No. 10/429,897, filed on May 5, 2003, which is a continuation of application No. 10/391,464, filed on Mar. 18, 2003, now Pat. No. 7,056,317, which is a continuation of application No. 09/902,369, filed on Jul. 9, 2001, now Pat. No. 6,540,739, which is a continuation of application No. 09/602,341, filed on Jun. 24, 2000, now Pat. No. 6,264,647.

(60) Provisional application No. 60/490,998, filed on Jul. 30, 2003.

(51) Int. Cl.
*B23B 31/113* (2006.01)

(52) U.S. Cl. ............... 279/93; 279/79; 279/80; 403/348; 403/349; 606/80

(58) Field of Classification Search ............... 279/79, 279/80, 93, 82, 89, 94; 403/348, 349, 109.3, 403/109.6, 378; 408/239 R; 606/80, 79, 606/81, 180
See application file for complete search history.

(56) References Cited

U.S. PATENT DOCUMENTS

| | | | | |
|---|---|---|---|---|
| 5,038,435 A | * | 8/1991 | Crawford et al. | 7/165 |
| 5,222,848 A | * | 6/1993 | Kuang-Wu | 408/239 R |
| 5,236,433 A | | 8/1993 | Salyer | |
| 5,349,940 A | * | 9/1994 | Takahashi et al. | 356/241.4 |
| 5,407,293 A | * | 4/1995 | Crainich | 403/322.1 |
| 5,464,300 A | * | 11/1995 | Crainich | 403/322.1 |
| 5,501,686 A | * | 3/1996 | Salyer | 606/79 |
| 5,582,607 A | * | 12/1996 | Lackman | 606/1 |
| 5,658,290 A | * | 8/1997 | Lechot | 606/80 |
| 5,817,096 A | * | 10/1998 | Salyer | 606/81 |
| 5,976,144 A | | 11/1999 | Fishbein et al. | |
| 5,980,170 A | * | 11/1999 | Salyer | 408/239 R |

(Continued)

FOREIGN PATENT DOCUMENTS

JP 05123336 A * 5/1993

*Primary Examiner*—Monica Carter
*Assistant Examiner*—Michael W. Talbot
(74) *Attorney, Agent, or Firm*—Moetteli & Associes SaRL (57) ABSTRACT

A surgical tool holder comprises a shank having first driveable end and second coupling end, the second end comprising a coupling device having interfaces for mating with corresponding structures on the inside of a hollow surgical tool, a first interface mating with a centering structure near a base end of the tool and a second interface mating with a second structure adjacent to a forward end of the tool, the tool being held in functional assembly to the shank by a releasable locking mechanism comprised of a locking sleeve slideably disposed about the shank, a spring biased against the coupling device by the locking sleeve, and a connection device retaining the locking sleeve in a fixed position during use, whereupon release of the connection device enables quick disassembly of the locking sleeve, spring and coupling device for cleaning and component sterilization.

21 Claims, 7 Drawing Sheets

U.S. PATENT DOCUMENTS

| | | | |
|---|---|---|---|
| 6,093,184 A * | 7/2000 | Campbell et al. | 606/1 |
| 6,126,359 A * | 10/2000 | Dittrich et al. | 403/349 |
| 6,129,732 A * | 10/2000 | Lechot | 606/80 |
| 6,168,600 B1 * | 1/2001 | Grace et al. | 606/81 |
| 6,277,121 B1 * | 8/2001 | Burkinshaw et al. | 606/80 |
| 6,409,732 B1 * | 6/2002 | Salyer | 606/91 |
| 6,475,221 B1 * | 11/2002 | White et al. | 606/80 |
| 6,506,000 B2 * | 1/2003 | Lechot | 407/35 |
| 6,540,739 B2 * | 4/2003 | Lechot | 606/1 |
| 6,875,217 B2 * | 4/2005 | Wolford | 606/81 |
| 2003/0078587 A1 * | 4/2003 | Lechot et al. | 606/81 |
| 2004/0097947 A1 * | 5/2004 | Wolford et al. | 606/80 |
| 2004/0249383 A1 * | 12/2004 | White et al. | 606/80 |
| 2005/0216020 A1 * | 9/2005 | Orton | 606/80 |
| 2005/0251145 A1 * | 11/2005 | Desarzens et al. | 606/80 |
| 2005/0261694 A1 * | 11/2005 | Orton et al. | 606/81 |

* cited by examiner

FIG. 6

HOLLOW SMALL DIAMETER TOOL HOLDER FOR SURGICAL USE

CROSS REFERENCE TO RELATED APPLICATIONS

This application claims priority to U.S. provisional application Ser. No. 60/490,998 filed Jul. 30, 2003 and is a continuation-in-part of U.S. patent application Ser. No. 10/429,897 filed May 5, 2003, entitled Hand-Held Tool Holder for Surgical Use, this in turn being a continuation-in-part of U.S. patent application Ser. No. 10/391,464, entitled Tool Holder for a Surgical Tool, filed on Mar. 18, 2003 now U.S. Pat. No. 7,056,317, which is in turn continuation of Ser. No. 09/902,369 filed on Jul. 9, 2001 and now U.S. Pat. No. 6,540,739 issued Apr. 1, 2003, which in turn is a continuation of Ser. No. 602,341 filed Jun. 24, 2000 and now U.S. Pat. No. 6,264,647 issued Jul. 24, 2001, the contents of which are incorporated herein by reference thereto.

BACKGROUND OF THE INVENTION

This invention relates to surgical tool holders, and more particularly, to holders of rotary surgical cutting tools.

Surgical tools and their respective holders have to be kept clean and sterile before any use in a hospital environment in order to minimize risk of transfer of disease or infection from patient to patient following the emergence of certain "prions" that are not killed by normal hospital sterilization and thus need to be physically removed through washing and rinsing. A surgical tool, for example for preparing for the fitting of a hip prosthesis, works in a medium which causes considerable soiling of the tool and of the tool holder. Despite the importance of doing so, the thorough cleaning of these devices is difficult. Surgical tool holders of the prior art are designed such that, in certain cases, washing and rinsing is generally not an effective way of cleaning the tool as some of the more resilient bugs are not destroyed. This is due to the small spaces left between component parts which allow only minimal access by cleaning agents.

Further, small diameter surgical cutting tools of the prior art are generally of solid construction. When cutting, such tools do not provide for the collection of bone chips for use in grafting.

What is needed therefore is a surgical tool holder which is quickly and simply disassembled for cleaning and sterilization. Still further, what is needed is a small diameter hollow tool that provides for the collection of bone chips for grafting.

SUMMARY OF THE INVENTION

The surgical tool holder of the invention has a shank having first driveable end and second coupling end, a coupling device mounted on the coupling end, and a locking mechanism. The coupling end has an interface thereon for receiving a tool. The coupling device has two interfaces for mating with corresponding structures on the inside of a hollow surgical tool. A first interface mates with a centering structure near a base end of the tool. A second interface mates with a second structure adjacent to a forward apex end of the tool. The locking mechanism in made up of a capture component, a spring, a locking sleeve which slides on the shank, and a locking device. The annular capture component is mounted so as to slide along the shank. The locking device cooperates with the capture component so as to lock the tool onto the interface. The spring biases the capture component in a locking direction and bears on the locking sleeve. The locking sleeve is disengageably lockable to the shank via a connection device. The connection device is preferably a bayonet mechanism.

The object of the invention is to enable quick disassembly for cleaning and component sterilization.

Another object is to hold a hollow tool capable of collecting bone chips for grafting.

BRIEF DESCRIPTION OF THE DRAWINGS

The attached drawings show embodiments of the invention by way of example.

DETAILED DESCRIPTION OF THE PREFERRED EMBODIMENT(S)

Figure 1:
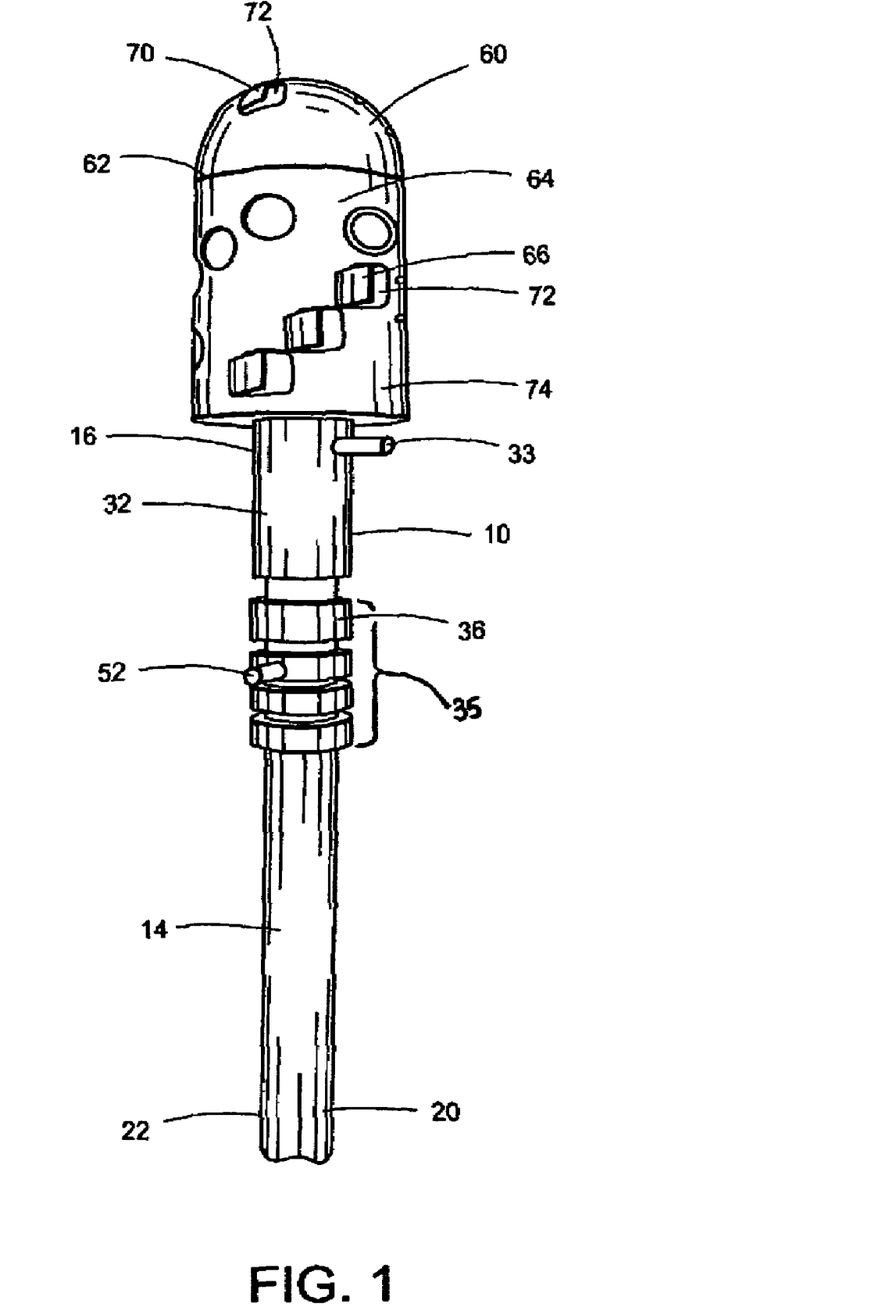
FIG. 1 is a side view of the tool holder of the invention, in a locked position.
Figure 4A:
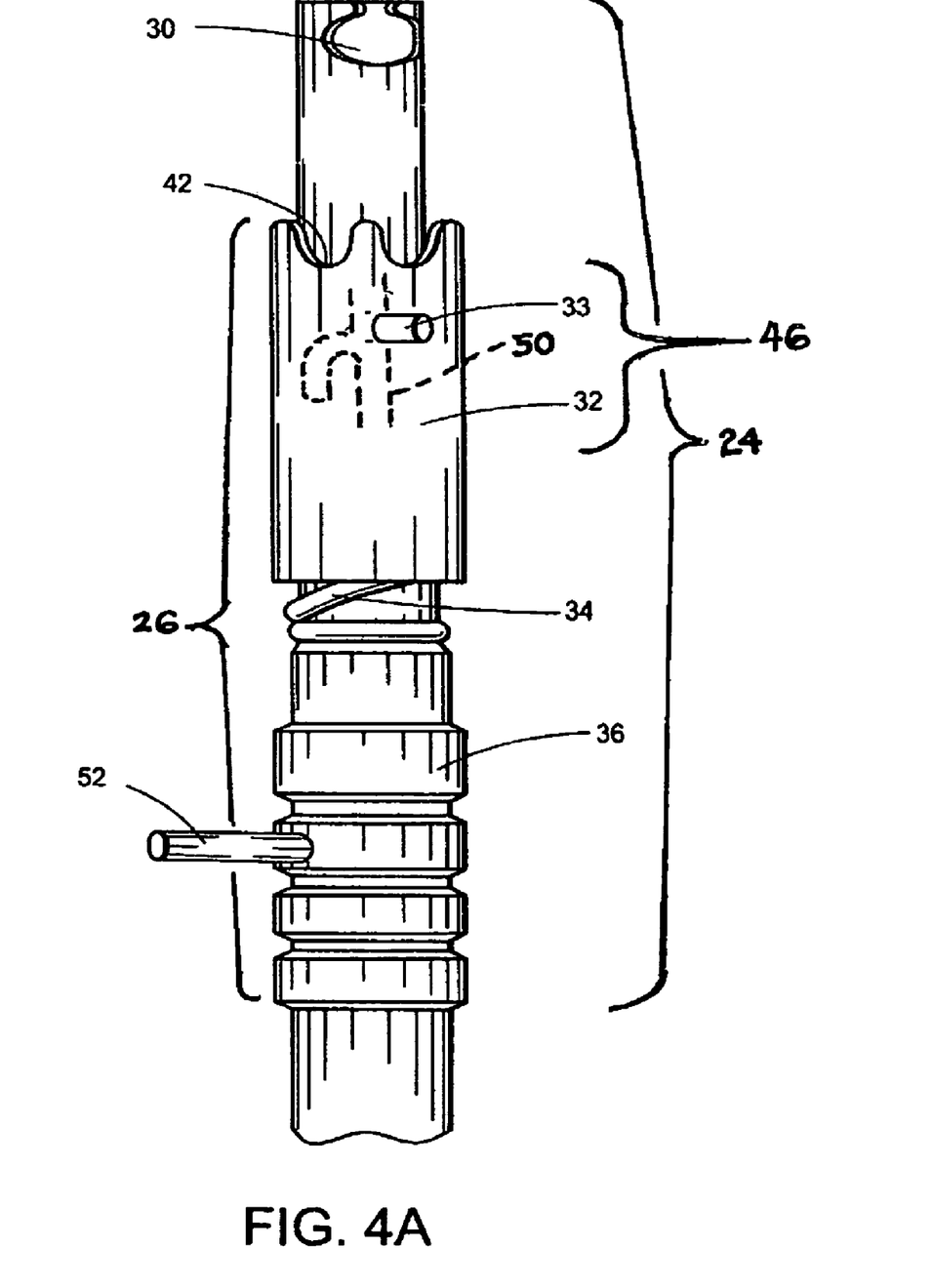
FIG. 4A is a side view of the holder of the invention, with the tool removed.

Referring now to FIG. 1, the hollow small diameter surgical tool holder 10 of the invention is shown. The holder 10 connects to a hollow surgical tool 12 to enable controlled manipulation of that tool. The holder 10 has a shank 14 having a coupling end 16, a drive interface 20 attached to an opposite end 22 of the shank, a coupling device 24 (shown in FIGS. 2B, 4A and 4B) and a locking mechanism 26. The coupling device 24 is located in the coupling end 16. The coupling device 24 is made up of two interfaces 42 and 30. The first interface 42 receives a centering structure made up of three, circumferentially spaced apart pins 40. The ends 80 of the pins 40 engage the first interfaces 42 in order to ensure that the tool 12 is retained in an axially aligned relationship with the holder 10. The second interface 30 is a a bayonet groove 30, formed transverse to the central axis of the shank 14, for receiving a cross bar 31 of the tool 12. The locking mechanism 26 is made up of a capture sleeve 32 in which the interfaces 42 are formed, a helical compression spring 34, and a connection device 35 made up of a locking sleeve 36 having a bayonet pin 52 which engages a bayonet slot 50. The capture sleeve 32, spring 34 and locking sleeve 36 slide alone the shank 14, the assembly locking in position when the locking sleeve is in a locking position.

The annular capture sleeve 32 mounts so as to slide along the shank 14. A key 33 passes through the capture sleeve 32 and into a longitudinal groove 35 (shown in FIG. 4B), thus preventing relative rotation of the sleeve 32 with respect to the shank 14. The centering pins 40 are disposed in the coupling end 16 of the shank 14 and received into annular recesses or interfaces 42 in the capture sleeve 32 when the capture sleeve is slid up the shank into a locked position, thus ensuring that the cross bar 31 is locked into the bayonet groove 30. The spring 34 biases the capture sleeve 32 in a locking direction and bears against the locking sleeve 36. The locking sleeve 36 is disengageably lockable to the coupling end 16 of the shank 14 via a bayonet mechanism 46 in which the pin 52 selectively engages the bayonet slot 50. The bayonet mechanism 46 includes a bayonet slot 50 and a locking pin 52. The bayonet slot 50 is cut in the coupling end 16 of the shank 14.

The locking sleeve 36 locks over the coupling end 16, and the shank 14 has a flat 37 so as to enable the locking pin 52 to freely slide along the shank 14 when the locking sleeve is unlocked and slid back along the shank, thereby providing cleaning access to all surfaces of the locking mechanism 26.

Figure 2A:
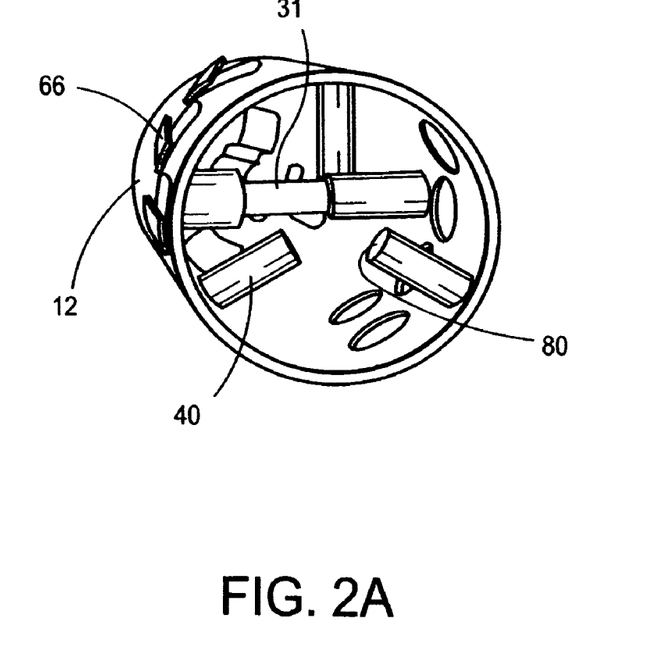
FIG. 2A is a perspective view of a hollow reamer tool which the invention is adapted to hold.
Figure 2B:
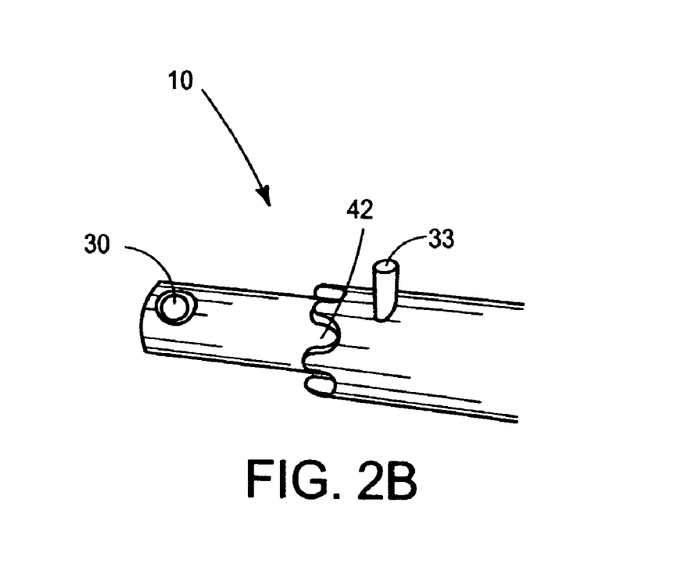
FIG. 2B is a perspective view of the coupling device of the invention.

The tool 12 is hollow along its length so as to provide a cavity to accumulate the bone chips during cutting, such bone chips being collectable for bone grafting.

The holder 10 is adapted to receive a hollow small diameter reamer 12 having a dome portion 60 connected via a weld at a seam 62 to a cylindrical portion 64. The reamer 12 has side cutting teeth 66 disposed in an ordered fashion about the cylindrical portion 64, and hemispherical cutting teeth 70 on the dome portion 60 of the reamer. Such teeth 66 and 70 are preceded by openings 72 to permit entry of chips in the hollow reamer 12 for collection.

Referring now to FIG. 2A, the centering pins 40 are disposed about the lower end or base 74 of the cylindrical portion 64, each pin terminating at a radial point about a base which circumscribes the shank 14 so as to center the shank as it enters the hollow reamer 12.

Figure 3:
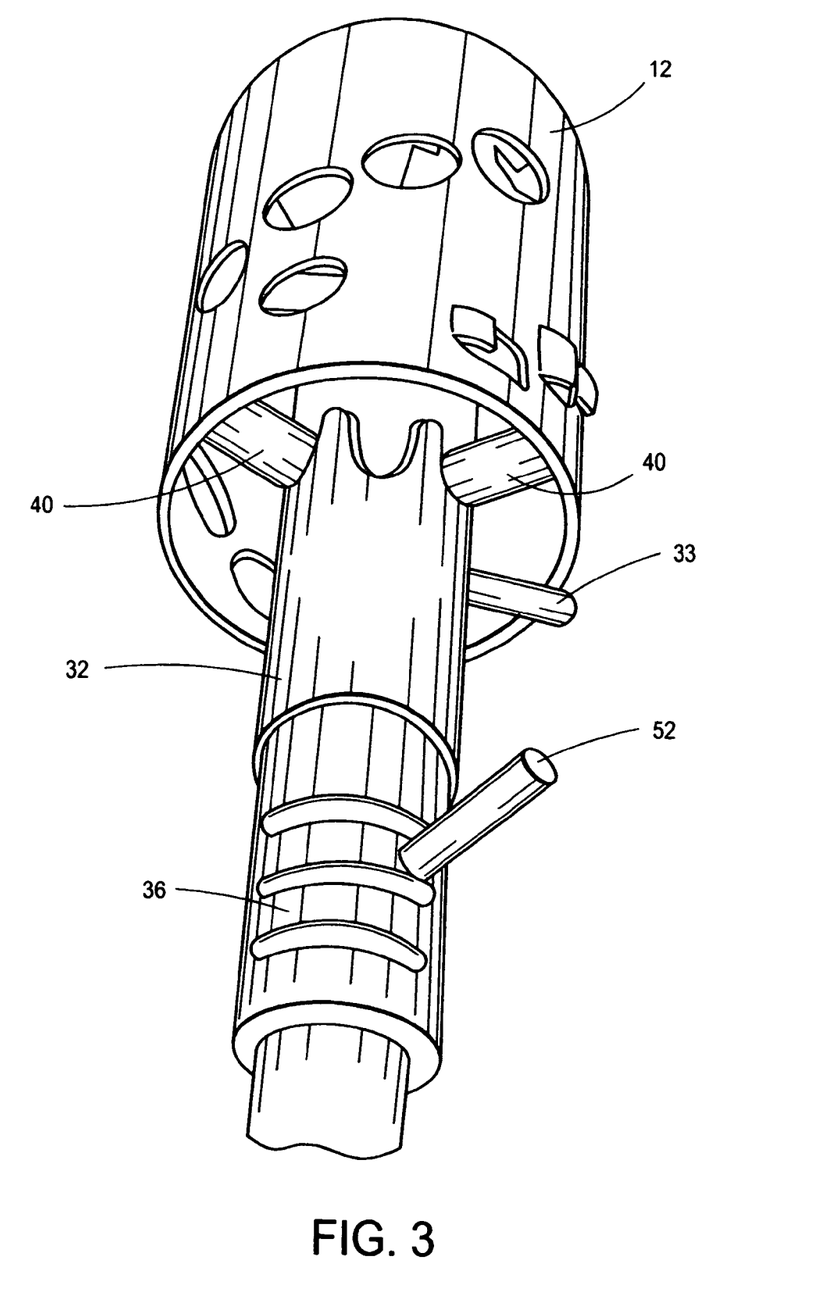
FIG. 3 is a perspective view of the tool holder, in a locked position, showing the interface between the tool and holder more clearly.

Referring in particular to FIG. 3, the ends 80 of the centering pins 40 contact the shank 14 as the tool 12 is placed over the coupling end 16 in order to center the shank upon installation of the tool. The cross bar 31 enters the bayonet groove 30 and the shank 14 is turned so as to move the cross bar into an end of the groove. The tool 12 is locked in this position when the capture sleeve 32 is raised into a position in which the recesses 42 of the capture sleeve engage the ends 80 of the centering pins 40.

Figure 4B:
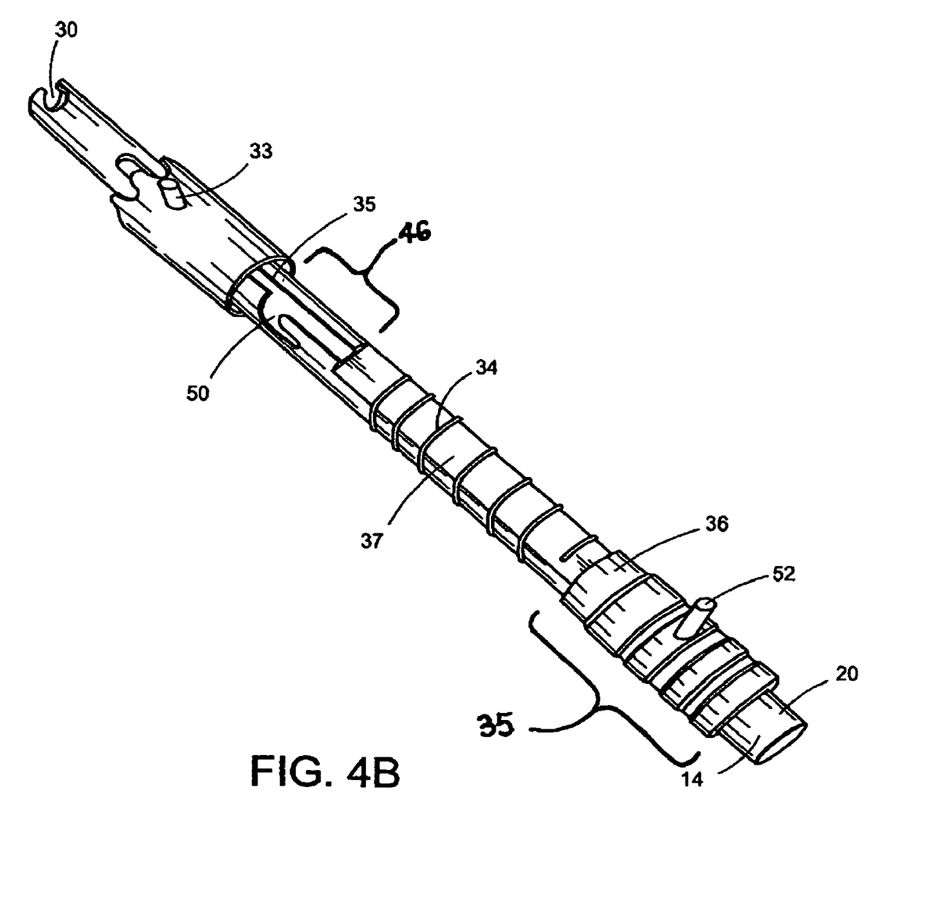
FIG. 4B is a perspective view of the holder of the invention, disassembled and ready for cleaning.

Referring now to FIG. 4B, the tool holder 10 is shown in an unlocked, partially disassembled position, ready for cleaning. To unlock the holder 10, the locking sleeve 36 is urged against the bias of spring 34 so as to lift it out of a bayonet seat 35, and then twisted so as to move the pin 52 out of the bayonet slot 50 in the coupling end 16 of the shank 14. The locking sleeve 36 may then be slid back along the shank 14, releasing the spring 34 and the sleeve 32, and thereby providing cleaning and sterilization access to the recesses that might otherwise not be accessible. The key 33 projects from the capture sleeve 32, thus providing a means of manipulating the sleeve 32 to lock the tool 12 in place.

Figure 5:
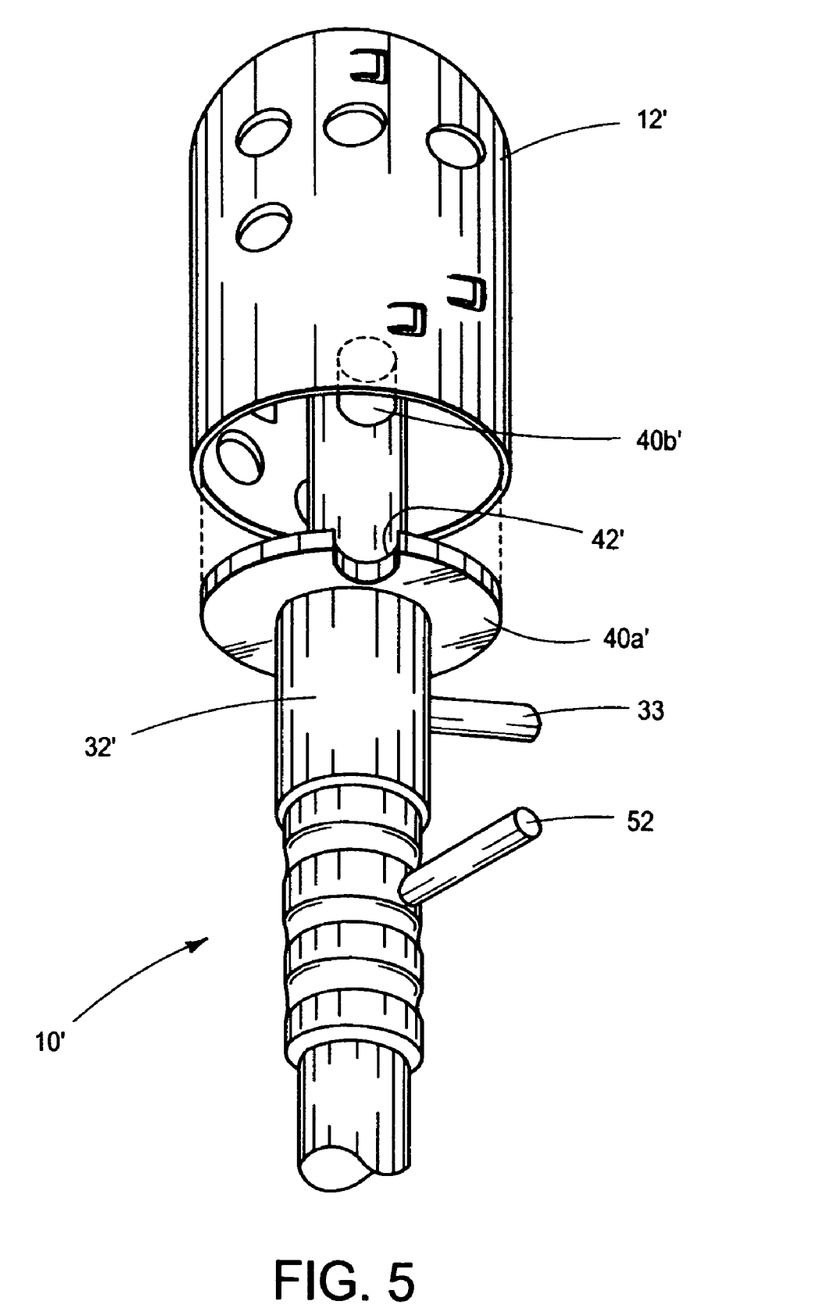
FIG. 5 is a perspective view of an alternate embodiment of the invention, having a keyed flange.

Referring now to FIG. 5, an alternate embodiment 10' is shown, in an unlocked, partially disassembled position. A flange 40a' on the capture sleeve 32' centers the capture sleeve on the tool 12'. A pin or locking interface 40b' on the tool 12' mates with a keyway interface 42' on the flange 40a' to lock the tool against relative rotation thereto. In this embodiment, the flange 40a' and pin 40b' together function in the same manner as the centering pins 40, by centering the capture sleeve 32' on the tool 12', and locking it against rotation.

Figure 6:
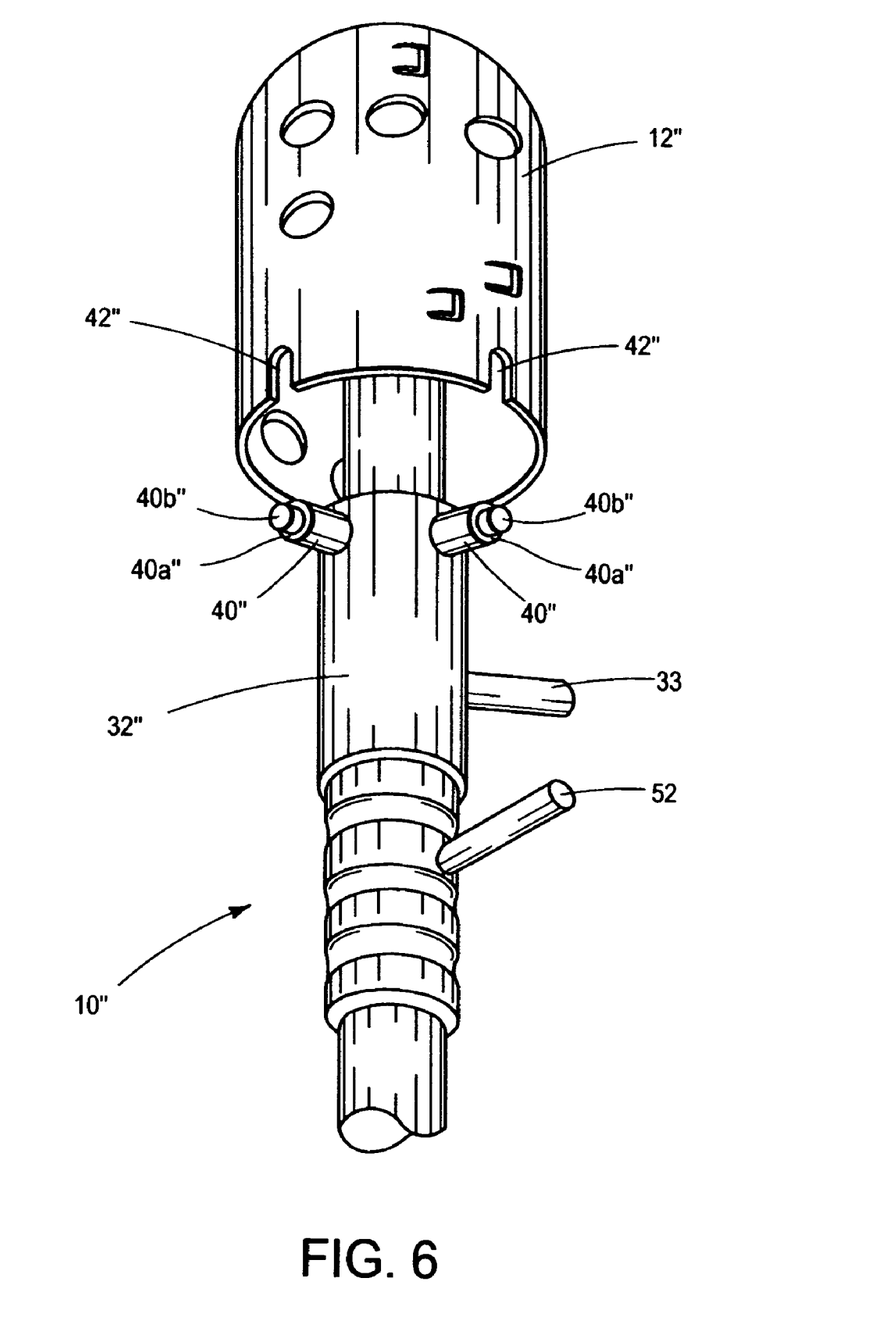
FIG. 6 is a perspective view of another alternate embodiment of the invention, having inverted pins and catches.

Referring now to FIG. 6, a second alternate embodiment 10" is shown in an unlocked, partially disassembled position. In place of the flange 40a', three centering pins 40" evenly spaced about the circumference of the capture sleeve 32" have ends 40b" which are received into the slots 42" on the tool 12", in order to lock the tool against relative rotation to the sleeve, and to center the tool with respect to the sleeve.

Shoulders 40a" having a diameter larger than the slots 42" ensure that the tool 12" cannot move transversely, thus firmly centering and locking the tool 12" against relative rotation to the sleeve 32". Play may of course be minimized by ensuring a close fit between the slots 42" and the outer diameters of the end portions 40b".

In an advantage of the invention, the bayonet mechanism 46 holds the locking sleeve 36 and thus the spring 34 in an operational position, as well as enabling quick disassembly for cleaning and component sterilization.

In another advantage of the invention, the holder is adapted to hold many different tool interfaces.

In another advantage, the holder 10 of the invention minimizes play and maximizes alignment with the turning axis.

In another advantage, the tool 12 enables the collection of chips in its central portion, thus providing bone chips for use in bone grafting.

Although illustrative embodiments of the invention have been shown and described a wide range of modification, change and substitution is contemplated in the foregoing disclosure and in some instances, some features of the present invention may be employed without a corresponding use of the other features. Further, the small hollow reamer is only an example of the types of tools that the invention may be adapted to hold. In fact, there are many different varieties of hollow tool configurations to which the invention is easily adaptable. The elastic devices used of course can be selected from a large variety of equivalents to a helical, compression spring, including, for example, leaf springs, flat springs, multiple compression springs, just to name a few. Still further, the connection mechanism can be substituted for a variety of connection mechanisms such as a threaded connection mechanism, a clasp, spring detents, or even magnetic retention devices. Accordingly it is appropriate that the appended claims be construed broadly and in a manner consistent with the scope of the invention.

What is claimed is:

1. A surgical tool holder comprising a shank having first driveable end and second coupling end, the second end comprising a coupling device having interfaces for mating with corresponding structures of a hollow surgical tool, a first interface mating with a centering structure near a base end of the tool and a second interface mating with a second structure adjacent to an opposite apex end of the tool and distal from the base end of the tool, the tool being held in functional assembly to the shank by a releasable locking mechanism comprised of a locking sleeve slideably disposed about the shank, a spring biased against the coupling device by the locking sleeve, and a connection device retaining the locking sleeve in a fixed position during use, whereupon release of the connection device enables quick removal of the locking sleeve, spring and coupling device for cleaning and component sterilization, and wherein the second interface is a transverse bayonet recess in the end of the shank and which mates with a cross bar.

2. The surgical tool holder of claim 1, wherein the coupling device comprises a locking device for locking the tool onto the shank.

3. The surgical tool holder of claim 2, wherein the locking device is disposed in the coupling end of the shank.

4. The surgical tool holder of claim 2, wherein the locking device comprises at least one centering shoulder structure keyed to the tool.

5. The surgical tool holder of claim 4, wherein the at least one centering structure is a flange.

6. The surgical tool holder of claim 4, wherein the centering shoulder structure comprises at least three circumferentially spaced apart centering pins, wherein the centering pins are keyed to contours in the capture sleeve.

7. The surgical tool holder of claim 1, wherein the coupling device comprises a capture sleeve against which the spring is biased by the locking sleeve, the capture sleeve being slideable along the shank, constrained to rotate with the shank and having at least one contour for mating with a corresponding contour on the centering structure.

8. The surgical tool holder of claim 7, wherein the corresponding contour on the centering structure is an exterior surface of a centering pin.

9. The surgical tool holder of claim 7, wherein the centering structure is a flange attached to a locking sleeve.

10. The surgical tool holder of claim 9, wherein the flange mates with a locking structure on the tool.

11. The surgical tool holder of claim 7, wherein when the locking sleeve is unlocked and slid back along the shank, cleaning access to all surfaces of the locking mechanism is facilitated.

12. The surgical tool holder of claim 7, wherein the locking device comprises contours in the capture sleeve which mate with three circumferentially spaced apart centering pins attached to the tool.

13. The surgical tool holder of claim 1, wherein a handle is attached to the connection device.

14. The surgical tool holder of claim 1, wherein the second interface is a recess in a forward end of the shank.

15. The surgical tool holder or claim 1, wherein the spring is a helical compression spring.

16. The surgical tool holder of claim 1, wherein the connection device comprises a bayonet mechanism.

17. The surgical tool holder of claim 16, wherein the bayonet mechanism is comprised of a bayonet slot and a locking pin.

18. The surgical tool holder of the claim 17, wherein the bayonet slot is disposed on the shank.

19. A small diameter hollow surgical tool for use with a tool holder, the tool having a first and second coupling interface and a centering structure near a base end of the tool, the tool holder comprising a shank having first driveable end and second coupling end, the second end comprising a coupling device having two interfaces for mating with the corresponding first and second coupling interface of the surgical tool, the first interface of the tool holder mating with the centering structure and the second interface of the tool holder mating with a cross bar distal from the base end and adjacent to an opposite apex end of the tool, and wherein the first interface of the tool holder is a flange which includes a locking interface that mates with a corresponding locking interface on the tool, to prevent relative rotation of the flange and the tool.

20. The surgical tool of claim 19, wherein the tool is held in functional assembly to the shank by a releasable locking mechanism comprised of a locking sleeve slideably disposed about the shank, a spring biased against the coupling device by the locking sleeve, and a connection device retaining the locking sleeve in a fixed position during use, whereupon release of the connection device enables easy removal of the locking sleeve, spring and coupling device for cleaning and component sterilization.

21. A surgical tool holder for mating with corresponding structures of a hollow surgical tool comprising:
   a shank having first driveable end and second coupling end,
      the second end comprising a coupling device having
         a first interface mating with a centering structure near a base end of the tool and
         a second interface mating with a second structure adjacent to an opposite apex end of the tool and distal from the base end of the tool,
         wherein the second interface is a transverse bayonet recess in the end of the shank and which mates with a cross bar, and
   the tool being held in functional assembly to the shank by
      a releasable locking mechanism comprised of
         a locking sleeve slideably disposed about the shank,
         a spring biased against the coupling device by the locking sleeve, and
         a connection device retaining the locking sleeve in a fixed position during use,
   whereupon release of the connection device enables quick removal of the locking sleeve, spring and coupling device for cleaning and component sterilization.

* * * * *

UNITED STATES PATENT AND TRADEMARK OFFICE
CERTIFICATE OF CORRECTION

PATENT NO.         : 7,229,078 B2                                Page 1 of 1
APPLICATION NO. : 10/901012
DATED              : June 12, 2007
INVENTOR(S)        : André Lechot It is certified that error appears in the above-identified patent and that said Letters Patent is hereby corrected as shown below:

In Col. 1, line 17, replace the phrase "a continuation of Ser. No. 602,341" with --a continuation of Ser. No. 09/602,341--.

In Col. 1, line 63, replace the phrase "The locking mechanism in made up" with --The locking mechanism is made up--.

In Col. 2, line 49, replace the phrase "The second interface 30 is a bayonet grove" with --The second interface 30 is a bayonet grove--.

In Col. 2, line 57, replace the phrase "alone the shank 14." with --along the shank 14,--.

Signed and Sealed this

Fourteenth Day of August, 2007

JON W. DUDAS
*Director of the United States Patent and Trademark Office*